US012766293B2

(12) United States Patent
Martin

(10) Patent No.: US 12,766,293 B2
(45) **Date of Patent: *Oct. 20, 2026**

(54) CATHETER HUB

(71) Applicant: Maduro Discovery, LLC, Campbell, CA (US)

(72) Inventor: Brian B. Martin, Santa Cruz, CA (US)

(73) Assignee: Maduro Discovery, LLC, Los Gatos, CA (US)

( * ) Notice: Subject to any disclaimer, the term of this patent is extended or adjusted under 35 U.S.C. 154(b) by 329 days.

This patent is subject to a terminal disclaimer.

(21) Appl. No.: 18/676,174

(22) Filed: May 28, 2024

(65) Prior Publication Data

US 2024/0307658 A1 Sep. 19, 2024

Related U.S. Application Data

(63) Continuation of application No. 18/359,604, filed on Jul. 26, 2023, now Pat. No. 12,029,865.

(60) Provisional application No. 63/369,840, filed on Jul. 29, 2022.

(51) Int. Cl.
*A61M 25/00* (2006.01)
*A61M 25/06* (2006.01)

(52) U.S. Cl.
CPC ..... *A61M 25/0097* (2013.01); *A61M 25/0637* (2013.01)

(58) Field of Classification Search
CPC ...................... A61M 25/0097; A61M 25/0637
See application file for complete search history.

(56) References Cited

U.S. PATENT DOCUMENTS

| | | | | |
|---|---|---|---|---|
| 4,366,817 | A | 1/1983 | Thomas | |
| 5,403,292 | A * | 4/1995 | Ju | A61L 29/049 604/527 |
| 6,228,073 | B1 | 5/2001 | Noone et al. | |
| 7,001,369 | B2 * | 2/2006 | Griffin | A61M 25/0054 604/524 |
| 7,717,865 | B2 | 5/2010 | Boutillette et al. | |
| 8,048,096 | B2 | 11/2011 | Wilkinson | |
| D653,337 | S | 1/2012 | Kampa et al. | |
| 8,372,057 | B2 | 2/2013 | Cude et al. | |
| 8,617,117 | B2 | 12/2013 | Popowski et al. | |
| 8,676,301 | B2 | 3/2014 | Coyle | |
| D760,386 | S | 6/2016 | Watanabe et al. | |
| D824,512 | S | 7/2018 | Laliberte et al. | |
| 10,675,010 | B2 | 6/2020 | Schwarz | |
| 10,874,830 | B2 | 12/2020 | Toth | |
| D923,784 | S | 6/2021 | Pupino et al. | |
| 12,029,865 | B2 * | 7/2024 | Martin | A61M 25/0097 |
| 2007/0151889 | A1 | 7/2007 | Brady | |
| 2013/0110082 | A1 | 5/2013 | Tekulve | |
| 2020/0391009 | A1 | 12/2020 | Martin | |
| 2024/0033480 | A1 | 2/2024 | Martin | |

FOREIGN PATENT DOCUMENTS

| | | |
|---|---|---|
| CN | 110236605 | 9/2019 |
| CN | 219847840 | 10/2023 |
| EP | 2174687 | 3/2016 |
| JP | 2012-200509 | 10/2012 |
| WO | WO 2024/026363 | 2/2024 |

* cited by examiner

*Primary Examiner* — Laura A Bouchelle
(74) *Attorney, Agent, or Firm* — Levine Bagade Han LLP

(57) ABSTRACT

Catheter hubs having one or more wings where a front and rear of the wing rotationally offset in a circumferential direction.

20 Claims, 7 Drawing Sheets

CATHETER HUB

CROSS-REFERENCE TO RELATED APPLICATIONS

This application is a continuation of U.S. patent application Ser. No. 18/359,604 filed Jul. 26, 2023, which claims the benefit of U.S. Provisional Patent Application No. 63/369,840 filed on Jul. 29, 2022, the entirety of which is incorporated by reference.

FIELD OF THE INVENTION

Improved hubs for use with catheters or other medical devices, where the hubs have at least one wing located on the hub body and extending between a near end located at the proximal portion and a far end located at the distal portion, where the near end is rotationally offset in a circumferential direction from the far end.

BACKGROUND OF THE INVENTION

Medical catheters allow physicians to apply a variety of different therapies within the body of a patient. Many catheters access remote regions of the human body for delivering diagnostic or therapeutic tools and/or agents to those sites. Alternatively, the catheter can comprise a shaft or support for a therapeutic working end (e.g., balloon, filter retriever, electrode, etc.). Some catheters, including but not limited to catheters for neurovascular use, are intended to be advanced from a main artery (e.g., a femoral or radial artery) through tortuous anatomy into a small cerebral vessel. As such, the catheter must be configured with varying structural traits due to the varying regions of the anatomy through which the catheter passes. Many times, the vascular pathways wind back upon themselves in a multi-looped path making it difficult for catheter design to meet the requirements demanded by the tortuous anatomy. Therefore, recent improvements in catheter design allow the pushing and manipulation of the catheter as it progresses through the body while still providing sufficient flexibility at the distal end to allow passage of the catheter tip through the loops and smaller blood vessels. The improvements in catheter tubing construction and technology drive a need to improve the design of catheter hubs, especially since improved catheter tubing construction improves the ability of a medical caregiver to navigate a catheter through tortuous vascular paths to distal regions in the vasculature.

FIG. 1A illustrates a traditional catheter 2 having a typical construction with a tubing 10 extending from a hub 20, where the tubing 10 can include a reinforcing member 12 within a wall 14 of the tubing. In additional variations, a liner (not shown) can be positioned within the tubing 10, and/or the reinforcing member 12 can be partially or fully embedded within either the wall 14 or liner. Typically, catheter hubs 20 include two protrusions, commonly referred to as wings 22, that allow for manipulation of the catheter 2. The catheter hub 20 can also include a connector 24 at a proximal end.

FIG. 1B shows a rear view of FIG. 1A taken along the lines of 1B-1B. As shown, the hub 20 allows fluid coupling of devices/substances with a catheter lumen 16. The wings 22 can extend on opposite sides of the hub 20. As noted above, in many cases, catheters must be advanced through tortuous anatomy with a decreasing vessel diameter, which requires torquing of the hub 20 using the wings 22 to rotate the catheter tubing 10 within a vessel. In such cases, when rotating the hubs 20 and/or wings 22 of a traditional catheter 2, a medical caregiver is limited to engaging the wings 22 on two sides of the hub.

Therefore, there remains a need for an improved hub design that complements the design of improved catheter tubing construction.

SUMMARY OF THE INVENTION

Figure 1A:
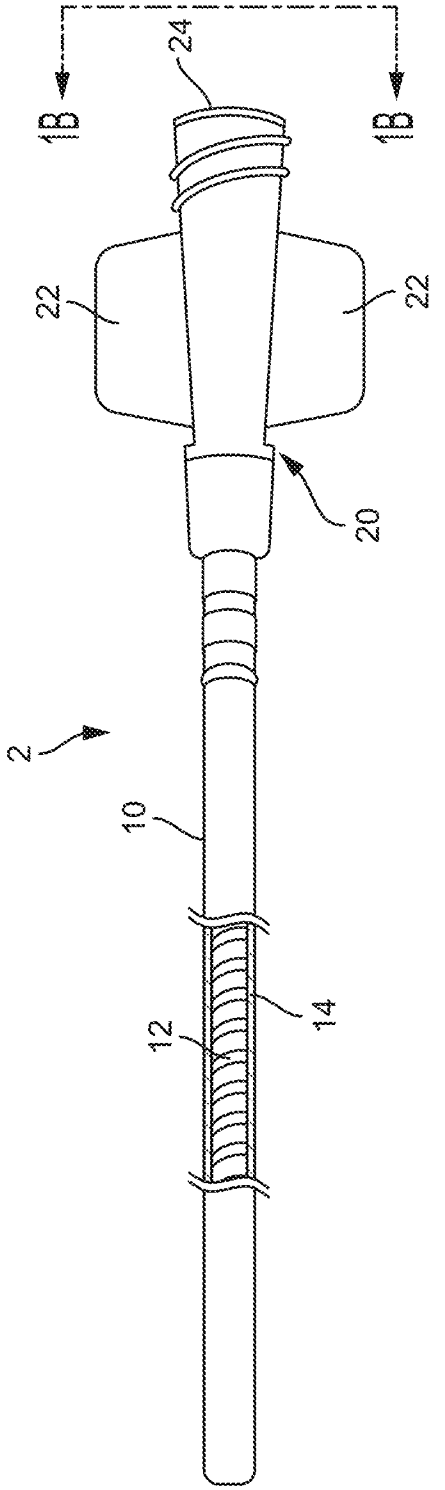
FIG. 1A illustrates a traditional catheter and hub construction
Figure 1B:
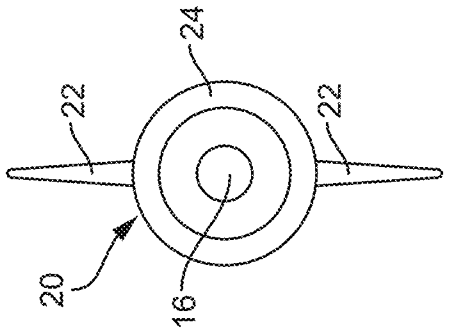
FIG. 1B shows a rear view of the catheter of FIG. 1A.

The present disclosure describes improved hubs used for medical devices. Variations of the improved hub can be used with a catheter, where the catheter includes a hub body having a proximal portion and a distal portion and an axis therebetween; a tubing extending from a distal end of the distal portion; and at least one wing located on the hub body and extending between a near end located at the proximal portion and a far end located at the distal portion, where the near end is rotationally offset in a circumferential direction from the far end. Providing wings with this configuration provides for devices that have a natural tendency for a user to rotate the catheter/medical device in the direction of a preferential wind of the catheter/device. The preferential wind results from the construction of the tubular device, so providing wings that match a rotational direction of the wind, in most cases, causes the user to turn the hub in the preferential direction of the preferential wind.

In an additional variation, the present disclosure relates to a hub for use with medical tubing, the hub including a hub body having a proximal portion and a distal portion, with an axis extending therebetween, wherein the hub is configured to be joined to the medical tubing at the distal portion; a plurality of wings located on the hub body, the plurality of wings including a first wing having a near end located at the proximal portion and a far end located at the distal portion, where the near end is rotationally offset from the far end in a circumferential direction along the hub body.

In some aspects, the techniques described herein relate to a hub for use with a medical tubing, the hub including a hub body having a proximal portion and a distal portion, with an axis extending therebetween, wherein the hub is configured to be joined to the medical tubing at the distal portion; a plurality of wings located on the hub body, the plurality of wings including a first wing having a near end located at the proximal portion and a far end located at the distal portion, where the near end is rotationally offset from the far end in a circumferential direction along the hub body.

The variations of the devices described herein relate to a catheter, wherein the at least one wing includes a plurality of wings each evenly spaced about a circumference of the hub body.

In additional variations, the plurality of wings includes at least a first wing and an adjacent wing, where the near end of the first wing and the far end of the adjacent wing are both rotationally offset from the far end of the first wing by a first angular distance.

In some variations of the hub configuration, a height of the at least one wing is greatest adjacent to the near end.

Variations of the hub also include a mid-section between the near end and the far end where a height of the at least one wing at the mid-section is less than a height of the near end and less than a height of the far end. The mid-section can be straight between the ends or curved.

In additional variations, the height of the near end is equal to the height of the far end. Hubs, according to the present design, can include a top surface of the wing having a concave profile at the midsection.

In some aspects, the hubs can be used with catheters that have tubing, which includes a structural component spirally extending along the tubing and having a winding direction and wherein the at least one wing includes a winding orientation from the near end to the far end. In some aspects, the winding direction and the winding orientation include a right-hand directional wind. Alternatively, the winding direction and the winding orientation can include a left-hand directional wind.

It is noted that the various design features of hubs and wings described herein can include combinations of the features into one or more hubs. For example, a single hub can include any number of unique wing designs. Alternatively, all of the wings on a hub can have the same design.

DETAILED DESCRIPTION

The improved hub configurations discussed herein can be used in a variety of devices. For purposes of illustration, one variation of the improved hub is used in distal access catheters that require torquing of the hub to navigate the catheter tube towards a desired location. Furthermore, in additional variations, the construction features of the present disclosure are not limited to in-dwelling medical devices and can be used for any device requiring tubing.

Figure 2:
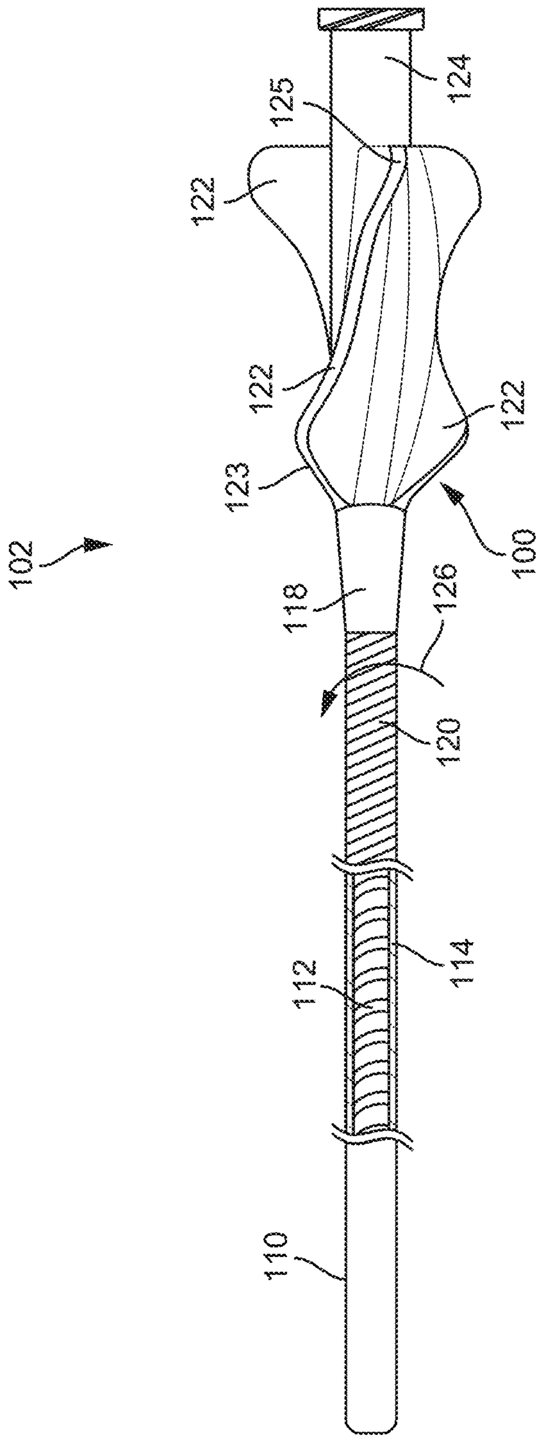
FIG. 2 shows an example of a catheter having an improved hub 100.

FIG. 2 shows an example of a catheter 102 having an improved hub 100. As shown, the catheter 102 includes a tubing 110 extending from the hub 100, where the tubing 110 can optionally include a reinforcing member 112 within or embedded in a wall 114 of the tubing 110. The illustrated catheter 102 can also include an optional strain relief 118 adjacent to the hub 100. The catheter 102 can also include an optional "winding" region 120. In some catheters, the construction of the catheter 102 results in a preferred torque direction, which can result from a directionality of the winding direction of the reinforcing member 112 (e.g., the winding of a coil) and/or the winding direction of a structure of the wall 114 of the catheter. In the example shown in FIG. 2, the winding direction of the reinforcing member 112 and "winding region" 120 is depicted by direction 126.

FIG. 2 illustrates the improved hub 100 having a number of wings 122 positioned around the circumference of the hub body, where each wing 122 comprises a twisted configuration where one end 123 of the wing 122 is rotationally offset in a circumferential direction from the opposite end 125 of the wing 122. As discussed in more detail below, variations of the device can match the direction of the twist with the preferred direction for torquing of the catheter, where the preferred direction of torquing of the catheter can be set by catheter construction. Therefore, the twisting of the wings 122 can serve as a tactile indicator to indicate the preferred direction for torquing of the catheter. While the illustrated examples show three wings 122, any number of wings are within the scope of this disclosure, including a single wing that is rotationally offset over 360 degrees of the hub body. While not shown, the hub 100 allows fluid coupling of devices/substances with a catheter lumen 116 extending in the tubing. In addition, the rotationally offset wings 122 provide a surface over substantially all of the catheter hub 100 as opposed to only on opposite sides of a conventional hub. This construction assists a caregiver when torquing the hub 100 using the wings 122 to rotate the catheter tubing 10 to navigate within a vessel.

Figure 3A:
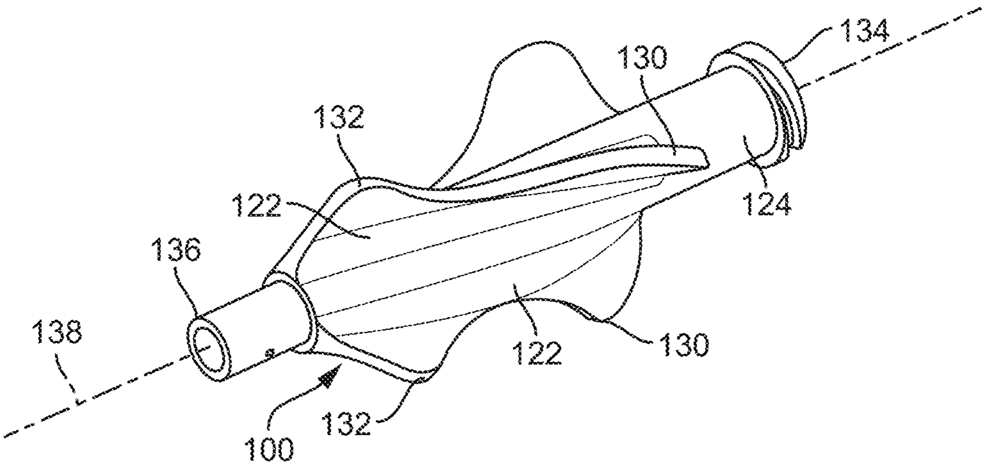
FIG. 3A shows an isometric view of the hub of FIG. 2 and illustrates rotationally offset wings.

FIG. 3A shows an isometric view of the hub 100 of FIG. 2 to better illustrate the rotationally offset wings 122. The wings 122 can comprise any flange, protrusion, or raised surface that allows for manipulation of the hub, as noted above. As shown, the hub 100 includes a proximal portion 134 adjacent to the connector 124 and a distal portion 136 that is coupled to a catheter or other tubing (not shown). An axis 138 runs between the proximal 134 and distal 136 portions of the hub. Wings 122 protrude from the hub 100 and include a near-end 130 located at or near the proximal portion 134 of the hub 100 and a far-end 132 at or near a distal portion 136 of the hub.

Figure 3B:
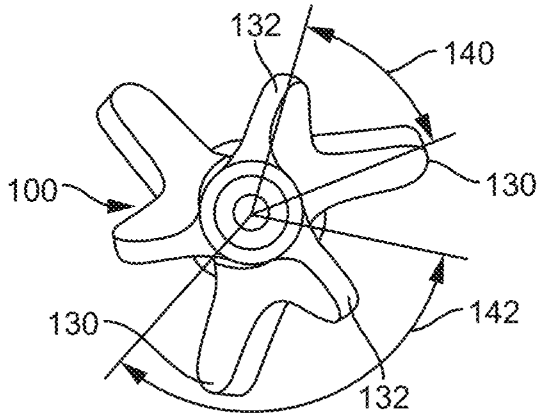
FIGS. 3B and 3C show respective front and side views of the hub of FIG. 3A.

FIG. 3B provides a front view of the hub 100 of FIG. 3A to illustrate the rotational offset of the wings 122. Angle 140 illustrates an angular offset in a circumferential direction between the near end 130 of the wing and the far end 132 at a peak of the near end 130 and far end 132. Angle 142 measures an angular offset (again in a circumferential direction) between a location where the near end 130 begins to protrude from the hub 100 surface to a second location where the far end 132 begins to protrude from the hub 100 surface. Clearly, the degree of rotational offset can vary based on hub design as well as where the offset is measured.

Figure 3C:
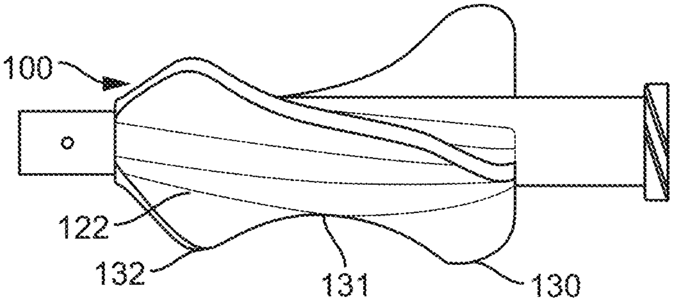

FIG. 3C illustrates another design feature of hubs 100 according to the disclosure. As shown, a wing 122 can include a near-end 130 separated from a far-end 132 by a mid-portion 131 that extends in a straight line between the ends, where the respective heights of the near and far ends 130, 132 are greater than a height of the mid-portion 131. By providing a mid-portion 131 with a height less than the near end, 130, and/or far-end 132 creates a concave structural feature that allows nesting of a finger or thumb of a caregiver while manipulating the hub 100. While all of the wings 122 on the hub 100 are shown to have the same design/profile, additional variations do not require all wings on a hub to have the same design/profile. In certain variations, one wing can have a unique profile to provide orientation information regarding the catheter.

Figure 4A:
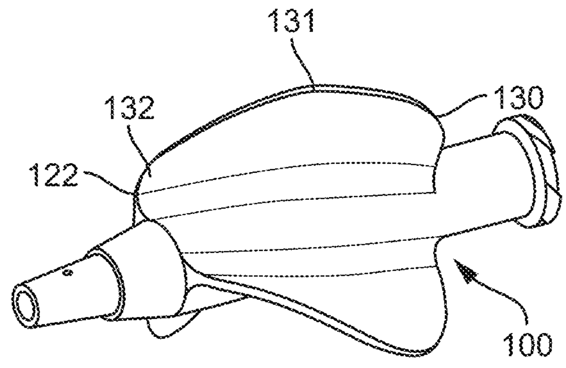
FIGS. 4A to 4C show another variation of a hub having wings 122 with the near end and far end rotationally offset in a circumferential direction.
Figure 4B:
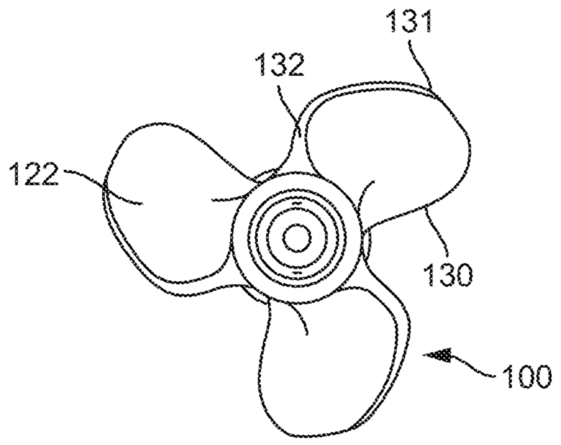
Figure 4C:
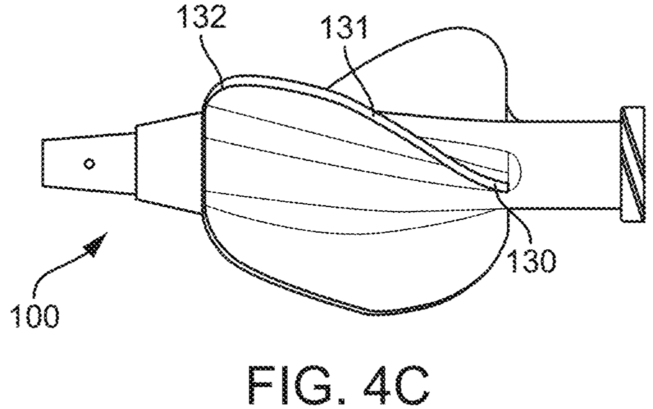

FIGS. 4A to 4C show another variation of a hub 100 having wings 122 with the near end 130 and far end 132 rotationally offset in a circumferential direction. In this variation, a height of the near-end 130 and far-end 132 is less than a height of a mid-portion 131 of the wing. In addition, as seen in FIG. 4C, the mid-portion 131 follows a curved profile between the near 130 and far 132 ends.

Figure 5A:
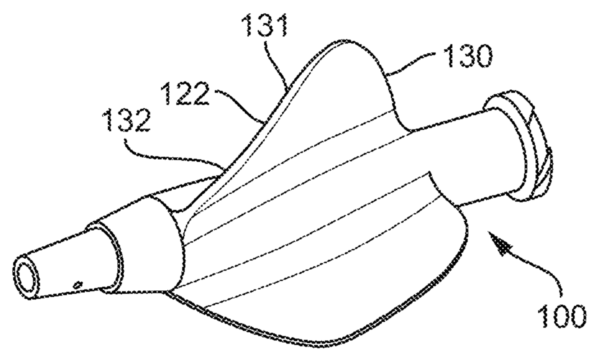
FIGS. 5A to 5C show respective isometric, front, and side views of a hub with wings having a left-handed winding direction where wings are rotationally offset in a leftward direction from the near end to the far end.
Figure 5B:
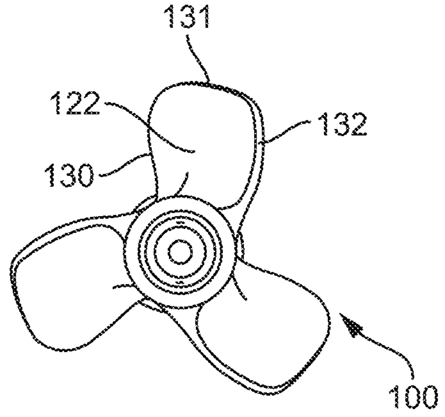
Figure 5C:
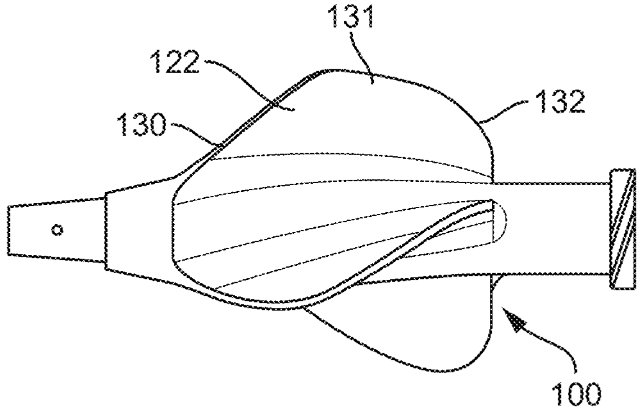

The variations of hubs 100 shown in the figures FIGS. 2, 3A to 3C, and 4A to 4C show hubs with a rotational offset in a right-hand direction, meaning when viewing the hub from the proximal end, the wing twists to the right. In contrast, FIGS. 5A to 5C show respective isometric, front, and side views of a hub 100 with wings 122 having a left-handed winding direction where the wing 122 is rotationally offset in a leftward direction from the near end 130 to the far end 132.

As noted above, any number of wings 122 is within the scope of the disclosure. In some variations, wings 122 will be spaced evenly about a circumference of the hub body. However, alternative variations can include rotationally offset hubs that are not evenly spaced about the circumference of the hub.

Figure 6A:
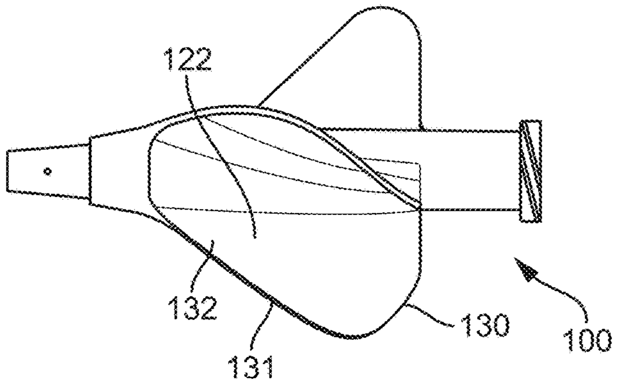
FIGS. 6A to 6D show side views of additional hubs having at least one wing having rotationally offset wings.
Figure 6B:
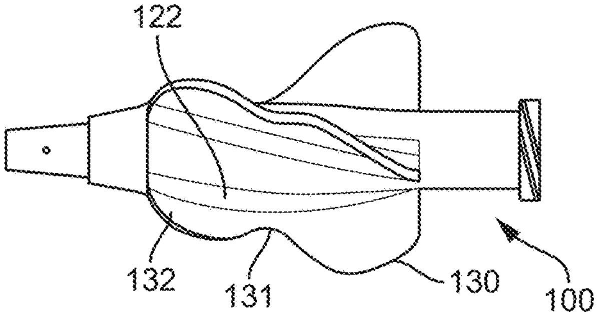
Figure 6C:
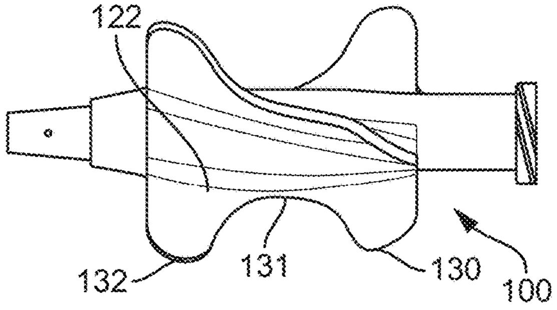
Figure 6D:
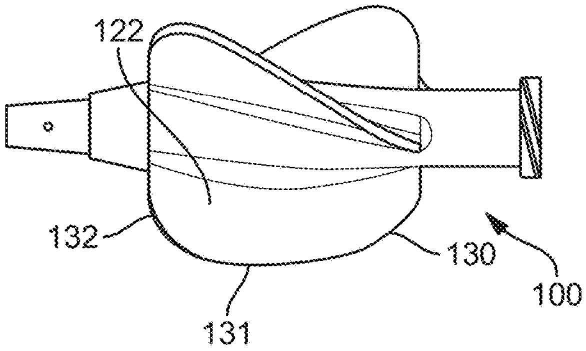

FIGS. 6A to 6D show side views of additional hubs 100 having at least one wing having ends 130 and 132 that are rotationally offset in a circumferential direction about the hub 100. FIG. 6A illustrates a wing 122 configured to decrease in height from the near end 130 to the far end 132. FIGS. 6B and 6C illustrate concave midportions 131 of the wing between ends 130 and 132, where FIG. 6C illustrates end portions 130 132 having the same height. FIG. 6D illustrates a hub 100 with a wing 122 having a midportion that extends in a straight profile between rotationally offset ends 130, 132. As for other details of the present invention, materials and manufacturing techniques may be employed within the level of those with skill in the relevant art. The same may hold true with respect to method-based aspects of the invention in terms of additional acts that are commonly or logically employed. In addition, though the invention has been described in reference to several examples, optionally incorporating various features, the invention is not to be limited to that which is described or indicated as contemplated with respect to each variation of the invention.

Figure 7A:
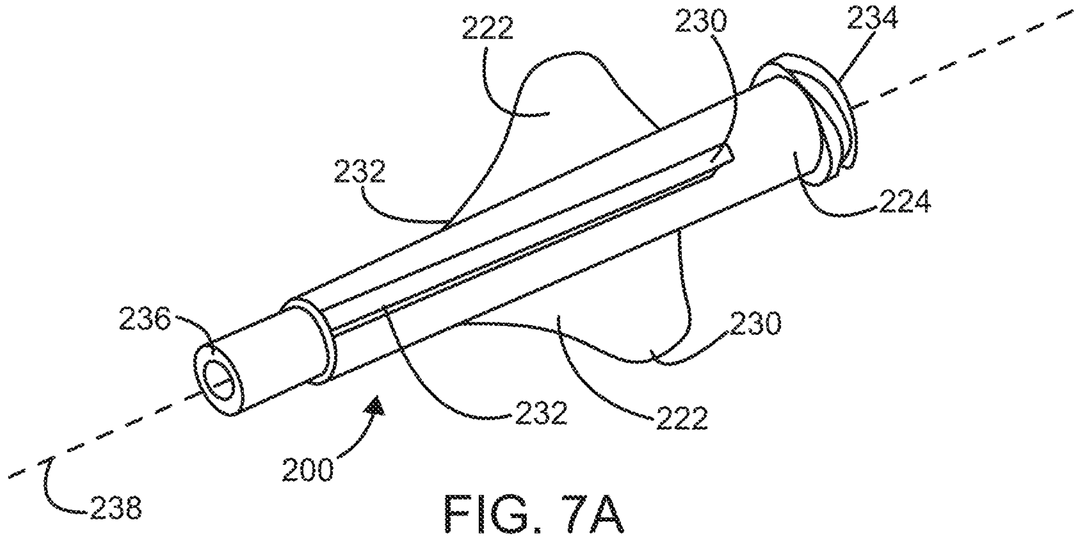
FIGS. 7A to 7C show respective isometric, front, and side views of a hub with straight flanges.

FIG. 7A shows an isometric view of another variation of a hub 200 with three wings 222, where the wings 222 are aligned with an axis 238 of the hub 200. It is contemplated that a hub can include an axially offset wing in combination with one or more axially aligned wings. Again the wings 222 can comprise any flange, protrusion, or raised surface that allows for manipulation of the hub 200, as noted above. The hub 200 includes a proximal portion 234 adjacent to the connector 224 and a distal portion 236 that is coupled to a catheter or other tubing (not shown). The axis 238 runs between the proximal 234 and distal 236 portions of the hub 200. Wings 222 protrude from the hub 200 and include a near-end 230 located at or near the proximal portion 234 of the hub 200 and a far-end 232 at or near a distal portion 236 of the hub 200.

Figure 7B:
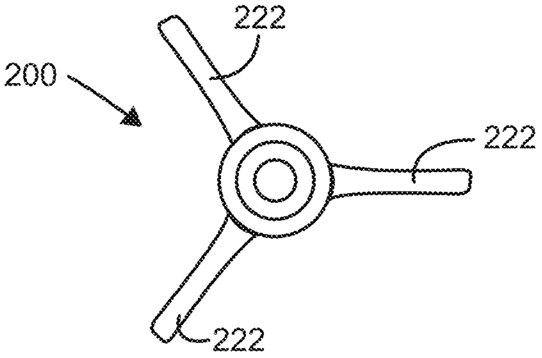
Figure 7C:
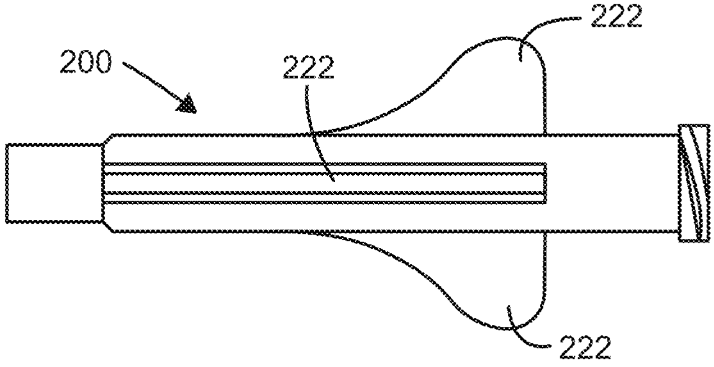

FIG. 7B provides a front view of the hub 200 of FIG. 7A to illustrate the wings 222 being axially aligned along the hub 200. FIG. 7C shows a side view of the hub 200. Although not illustrated, for the wings the respective heights of the near and far ends of the wings 222 are different than a height of the mid-portion. Providing a mid-portion with a reduced height relative to the near end and/or far end creates a concave structural feature that allows nesting of a finger or thumb of a caregiver while manipulating the hub 200. While all of the wings 222 on the hub 200 are shown to have the same design/profile, additional variations do not require all wings on a hub to have the same design/profile. In certain variations, one wing can have a unique profile to provide orientation information regarding the catheter.

Various changes may be made to the invention described, and equivalents (whether recited herein or not included for the sake of some brevity) may be substituted without departing from the true spirit and scope of the invention. Also, any optional feature of the inventive variations may be set forth and claimed independently or in combination with any one or more of the features described herein. Accordingly, the invention contemplates combinations of various aspects of the embodiments or combinations of the embodiments themselves, where possible. Reference to a singular item includes the possibility that there are plural of the same items present. More specifically, as used herein and in the appended claims, the singular forms "a," "and," "said," and "the" include plural references unless the context clearly dictates otherwise.

It is important to note that, where possible, aspects of the various described embodiments or the embodiments themselves can be combined where such combinations are intended to be within the scope of this disclosure.

I claim:

1. A catheter comprising:

a hub body having a proximal portion and a distal portion, with an axis therebetween;

a tubing extending from a distal end of the distal portion of the hub body; and a plurality of wings on the hub body, the plurality of wings extending in a twisted profile about the hub body between the proximal portion and the distal portion such that for each wing of the plurality of wings a near end is circumferentially offset from a far end.

2. The catheter of claim 1, wherein the plurality of wings are evenly spaced about a circumference of the hub body.

3. The catheter of claim 2, wherein the plurality of wings comprises at least a first wing and an adjacent wing, where the near end of the first wing and the far end of the adjacent wing are both rotationally offset from the far end of the first wing by a first angular distance.

4. The catheter of claim 1 further comprising a threaded portion located at a proximal end of the proximal portion.

5. The catheter of claim 1, wherein a height of the plurality of wings is greatest adjacent to the near end.

6. The catheter of claim 1, where a height of at least one wing of the plurality of wings includes a mid-section that is less than a height of the near end and less than a height of the far end of the at least one wing.

7. The catheter of claim 6, where a top surface of the at least one wing is concave at the mid-section.

8. The catheter of claim 6, wherein the at least one wing is curved between the near end and the far end.

9. The catheter of claim 6, wherein the at least one wing is straight from the near end to the far end.

10. The catheter of claim 1, wherein the tubing comprises a structural component spirally extending along the tubing and having a winding direction and wherein the plurality of wings comprises a winding orientation from the near end to the far end.

11. The catheter of claim 10, wherein the winding direction and the winding orientation comprise a right-hand directional wind.

12. The catheter of claim 10, wherein the winding direction and the winding orientation comprise a left-hand directional wind.

13. A hub for use with a medical tubing, the hub comprising:

a hub body having a proximal portion and a distal portion, with an axis extending therebetween, wherein the hub is configured to be joined to the medical tubing at the distal portion;

a plurality of wings on the hub body, the plurality of wings extending in a twisted profile about the hub body between the proximal portion and the distal portion such that for each wing of the plurality of wings a near end is circumferentially offset from a far end.

14. The hub of claim 13, wherein the plurality of wings are evenly spaced about a circumference of the hub body.

15. The hub of claim 14, wherein the plurality of wings comprises at least a first wing and an adjacent wing, where the near end of the first wing and the far end of the adjacent wing are both rotationally offset from the far end of the first wing by a first angular distance.

16. The hub of claim 13, further comprising a threaded portion located at a proximal end the proximal portion.

17. The hub of claim 13, wherein a height of each of the plurality of wings is greatest adjacent to the near end.

18. The hub of claim 13, where each of the plurality of wings includes a mid-section between the near end and the far end.

19. The hub of claim 18, where a top surface of each of the plurality of wings is concave at the mid-section.

20. The hub of claim 18, wherein at least one wing of the plurality of wings is curved between the near end and the far end.

* * * * *